(12) United States Patent
La Placa et al.

(10) Patent No.: US 8,550,087 B2
(45) Date of Patent: Oct. 8, 2013

(54) IMPLANT DELIVERY DEVICE WITH EXPANDING TIP

(75) Inventors: Matthew La Placa, Cumberland, RI (US); David Callaghan, Mansfield, MA (US); Mark Putnam, Weymounth, MA (US); Jeffrey Model, Cambridge, MA (US)

(73) Assignee: Hologic, Inc., Marlborough, MA (US)

( * ) Notice: Subject to any disclaimer, the term of this patent is extended or adjusted under 35 U.S.C. 154(b) by 218 days.

(21) Appl. No.: 12/940,698

(22) Filed: Nov. 5, 2010

(65) Prior Publication Data

US 2012/0111336 A1    May 10, 2012

(51) Int. Cl.
*A61F 6/06* (2006.01)
*A61M 29/00* (2006.01)

(52) U.S. Cl.
USPC .......................... 128/831; 128/830; 606/193

(58) Field of Classification Search
USPC .......... 128/830–833, 887; 604/19, 48, 57, 59, 604/60, 61; 623/1.11, 1.12, 1.27; 606/191–193, 197–198
See application file for complete search history.

(56) References Cited

U.S. PATENT DOCUMENTS

| | | | |
|---|---|---|---|
| 6,676,693 B1 * | 1/2004 | Belding et al. | 623/1.11 |
| 7,651,520 B2 * | 1/2010 | Fischell et al. | 623/1.11 |
| 8,187,267 B2 * | 5/2012 | Pappone et al. | 606/41 |
| 2001/0034549 A1 * | 10/2001 | Bartholf et al. | 623/1.12 |
| 2002/0188247 A1 * | 12/2002 | Peery | 604/60 |
| 2004/0255958 A1 * | 12/2004 | Harrington et al. | 128/898 |
| 2009/0062726 A1 * | 3/2009 | Ford et al. | 604/57 |

\* cited by examiner

*Primary Examiner* — Patricia Bianco
*Assistant Examiner* — Ophelia A Hawthorne
(74) *Attorney, Agent, or Firm* — Vista IP Law Group LLP

(57) ABSTRACT

Devices and methods are disclosed for the delivery of an implant into small bodily spaces. The delivery devices include an expandable portion configured for placement within such bodily spaces and subsequent expansion to facilitate the delivery of the implant.

16 Claims, 3 Drawing Sheets

IMPLANT DELIVERY DEVICE WITH EXPANDING TIP

FIELD OF THE INVENTION

The present invention relates to low profile devices that are useful for the delivery of one or more implants into small spaces within the body of a patient, and more particularly, to devices that may be used to deliver an implant into a fallopian tube.

BACKGROUND

It is often desired or necessary for medical reasons to deliver an implant into a bodily opening or cavity, such as a bodily lumen, such as those found within the vascular, urogenital, and gastrointestinal systems. For example, stents may be delivered into any of these systems, embolic implants may delivered into blood vessels, and occlusion implants may be delivered into the fallopian tubes for sterilization purposes.

An example of an occlusive implant that is placed within the fallopian tubes for sterilization purposes is the Adiana® Permanent Contraception system (Hologic, Inc., Marlborough, Mass.). To use this system, a flexible delivery catheter is passed through the vagina and cervix and into each fallopian tube to deliver a low level of radiofrequency energy, followed by the delivery of a small occlusion implant. Implants are usually placed in the uterotubal junction, the narrowest part of the fallopian tubes. Such implants and procedures are described, for example, in U.S. Pat. No. 7,220,259, which is incorporated herein by reference.

Many implants provided by multiple vendors, including occlusion implants, embolics, and stents, are often configured or made from polymeric materials that allow for the compression of these implants into small profiles so that they may fit within the dimensions of their respective delivery devices. After the delivery device is positioned to a target location within the patient, the implant is extruded or otherwise released from the delivery device such that it may self-expand or otherwise expand from its reduced, delivery configuration into an expanded, working configuration to thereby keep the implant at the target location within the body.

Because many implants are loaded into a delivery device at the point of manufacture rather than at the point of use, they are consequently kept in a reduced configuration within the confines of the delivery device during sterilization, shipping, and storage. During such time, the materials used in such implants may undergo stress relaxation or other changes to mechanical properties that result from being held in a reduced configuration. The result is that many implants have a short permissible shelf lives and temperature exposure limitations.

It is an object of the present invention to provide for delivery devices and associated methods that allow for implants to be sterilized, shipped, and stored for extended periods of time and/or at elevated temperatures without adversely affecting their properties or working function. It is a further object of the present invention to provide for an implant delivery device that allows for device placement within confined bodily lumens or spaces, such as the uterotubal junction, and subsequent expansion while within such confined lumens or spaces.

SUMMARY OF THE INVENTION

In one aspect, the present invention comprises a device for the delivery of an implant into the body of a patient.

In another aspect, the present invention comprises a kit that includes an implant pre-loaded in a delivery device.

In yet another aspect, the present invention comprises a method of treating a patient by delivering an implant into the body of a patient by using the delivery devices of the present invention.

In certain embodiments, the present invention comprises a device for the delivery of an implant into a patient's body. The device comprises an elongated member having proximal and distal openings, and a continuous open space or lumen extending between the openings. The device preferably includes a non-expandable portion extending to the proximal opening, and an expandable portion extending to the distal opening. The expandable portion has a first cross-sectional outer dimension and a first cross-sectional inner dimension when in an unexpanded condition, and a second cross-sectional outer dimension and a second cross-sectional inner dimension when in an expanded condition. Both the second inner and outer cross-sectional dimensions are greater than the respective first inner and outer cross-sectional dimensions. The first cross-sectional inner dimension of the expandable portion is less than a cross-sectional dimension of the implant to be delivered into the patient's body.

DESCRIPTION OF THE PREFERRED EMBODIMENTS

Figure 1:
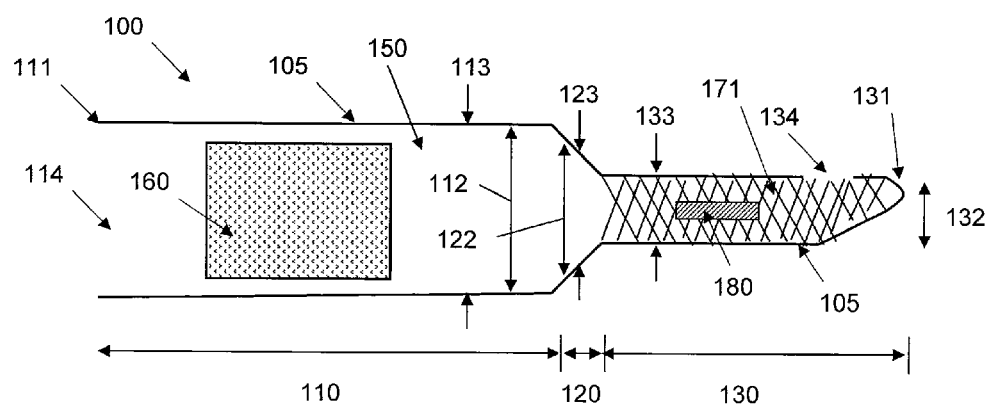
FIG. 1 is a cross-sectional view of an implant delivery device having an expandable, braided distal section, in accordance with an embodiment of the present invention.

The present invention provides devices that allow for the delivery of implants into small bodily spaces, such as bodily openings, cavities, and lumens, such as the uterotubal junction and/or fallopian tubes. At least a portion of the delivery devices of the present invention have small dimensional characteristics, or a so-called low profile, that permit their introduction into such small bodily spaces. Such portion of the delivery devices is expandable following introduction into the body to allow for the delivery of one or more implants that may have dimensional characteristics that are generally larger than the unexpanded dimensions of the delivery device. The delivery devices of the present invention allow implants, such as compressible implants, to be kept in a substantially uncompressed configuration prior to and during delivery into a patient. Because the compressible implants are kept in a substantially uncompressed configuration, they can be sterilized, shipped and stored for relatively long time periods and at high temperatures while maintaining its desired configuration upon delivery. In contrast, compressible implants that are sterilized, shipped and stored in substantially compressed configurations within the confines of conventional implant delivery devices have short permissible shelf lives and temperature exposure limitations in order to minimize the risk that they will undergo stress relaxation prior to delivery into a patient.

The present invention is described with specific reference to an occlusive implant that is placed within the fallopian tubes for sterilization purposes. It should be recognized, however, that the devices and methods of the present invention are equally applicable to the delivery of any implant into small bodily spaces. Non-limiting examples of such implants include self-expanding polymeric stents, filters, and polymeric embolics and other occlusive implants. It should also be recognized that the present invention is equally applicable to compressible, non-compressible, expandable, and non-expandable implants.

In one embodiment, the present invention includes a device for the delivery of a compressible implant into a bodily lumen. As shown in the cross-sectional side view of FIG. 1, the delivery device 100 generally comprises a proximal section 110, a distal section 130, and an optional intermediate section 120 between the proximal and distal sections 110, 130. The distal section 130 is intended to be insertable into the bodily lumen, and terminates in a distal tip 131. The proximal section 110 terminates in a proximal end 111, which is intended to extend outside of the body during use. The outer configuration of delivery device 100 and its sections are preferably cylindrical. It should be noted that none of the drawings herein are drawn to scale.

Each of the proximal, distal, and intermediate sections 110, 130, 120 is characterized by a respective inner dimension, preferably a diameter, noted as dimensions 112, 132, and 122. Each section is also characterized by a respective outer dimension 113, 133, and 123, preferably a diameter, the size of which is sum of each respective inner dimension 112, 132, and 122 and twice the width of the side wall 105 of each respective section. In all embodiments of the invention, the distal section 130 represents an expandable portion of the device 100, by self-expansion or by the application of a force, as described further herein. In the configuration shown in FIG. 1, the distal section 130 is in its unexpanded condition. Preferably, the proximal section 110 and optional intermediate section 120 are non-expandable and are therefore of substantially constant dimensions, i.e., respective cross-sectional inner and outer dimensions. When the distal section 130 is in an unexpanded condition, the inner and outer dimensions 132, 133 of the distal section 130 are less than the respective inner and outer dimensions 112, 113 of the proximal section 110. Also when the distal section 130 is in an unexpanded condition, the inner dimension 132 is preferably less than a cross sectional dimension of implant 160, but it may also be substantially the same as a cross sectional dimension of implant 160. When the distal section 130 is in an expanded condition, the inner and outer dimensions 132, 133 of the distal section will be greater than when in the unexpanded condition, and may be less than, approximately the same as, or larger than the inner and outer dimensions 112, 113 of the proximal section 110 or the inner and outer dimensions 122, 123 of the intermediate section 120.

The delivery device 100 includes an opening 114 in the proximal section, and another opening 134 in the distal section to provide access to a lumen or continuous open space 150 that extends within the inner diameters of the proximal, distal, and optional intermediate sections. As used herein, "lumen" is not intended to convey any particular cross-sectional shape, but is used synonymously with "continuous open space" or the like. While the opening 134 is preferably on a side wall of the distal section 130 as shown in FIG. 1, it is alternatively located at the tip of the distal end 131. In either event, the opening 134 is referred to as a "distal opening." Locating the opening 134 on the side wall instead of the tip of the distal end 131 allows the tip to be rounded, or preferably in the form of a "ball tip" to minimize trauma to tissue as the delivery device 100 is advanced through tissue or within a bodily lumen. The opening 114 in the proximal section allows for the loading of an implant 160 into the delivery device 100, while the opening 134 in the distal section allows for the delivery of the implant 160 into the patient.

Figure 2:
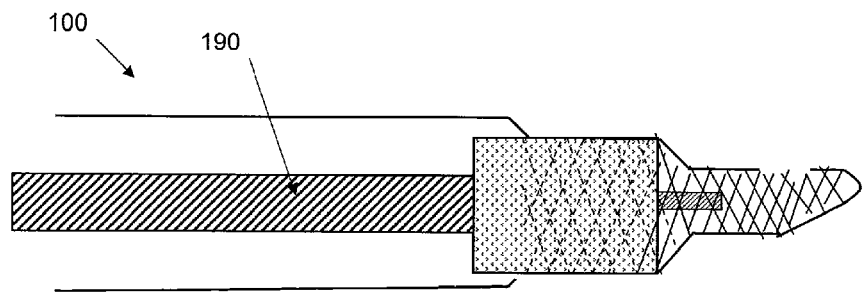
FIG. 2 is a cross-sectional view of an implant delivery device in which the implant is advancing into the expandable distal portion of the device, in accordance with an embodiment of the present invention.
Figure 3:
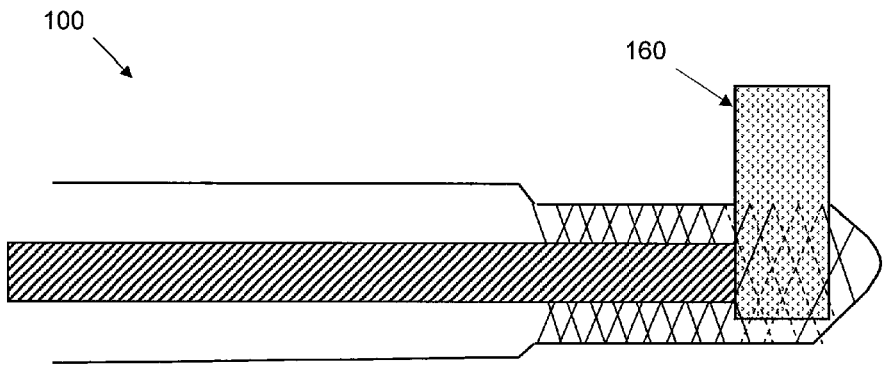
FIG. 3 is a cross-sectional view of an implant delivery device in which the implant is being extruded into a patient, in accordance with an embodiment of the present invention.

The expandable distal section 130 extends to and includes the distal opening 134. In a preferred embodiment, the distal section 130 is a woven or braided structure of polymeric or metallic strands 171 that will expand upon advancement of the implant 160 into the distal section 130 due to the force exerted on the sidewall 105 of the distal section 130 by the implant itself. This is shown in FIGS. 2 and 3, which illustrate the expansion of the distal section 130 upon the advancement of implant 160 through the distal section 130 and out of the distal opening 134. In a preferred embodiment, when the expandable distal section 130 is in an expanded condition, it at least partially contacts surrounding tissue and exerts a force on such tissue. For example, the expandable distal section 130 may expand a surrounding bodily lumen such as a fallopian tube prior to and/or during the delivery of implant 160. While not wishing to be bound by theory, the inventors believe that such expansion may enhance the ability of surrounding tissue to hold the implant 160 in place following delivery.

Figure 4A:
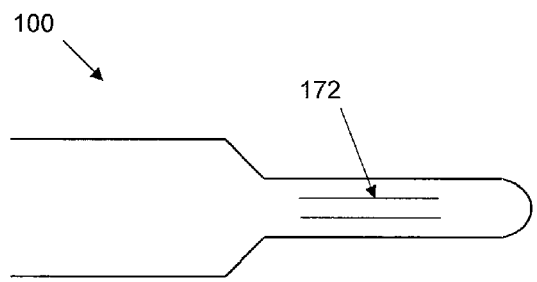
FIGS. 4a and 4b are perspective views of an implant delivery device having an expandable distal section with longitudinal slits or slots, in accordance with an embodiment of the present invention.
Figure 4B:
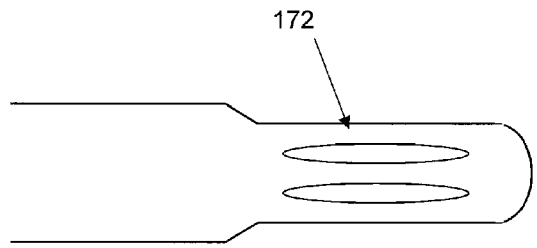
Figure 5A:
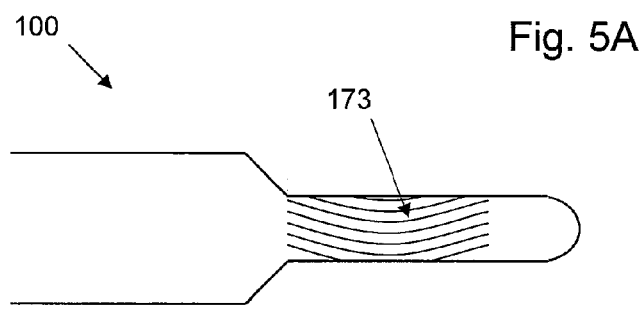
FIGS. 5a and 5b are perspective views of an implant delivery device having an expandable distal section with an annular balloon, in accordance with an embodiment of the present invention.
Figure 5B:
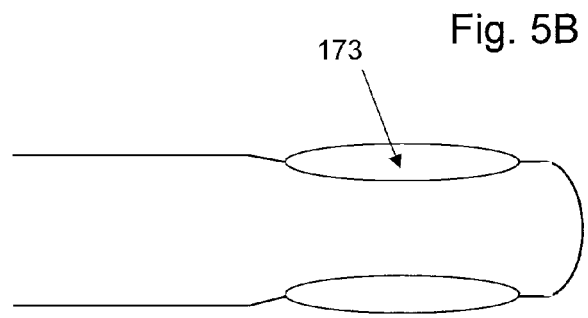

In other embodiments, the distal section 130 includes slits or slots 172 as shown in FIG. 4a that open when the distal section 130 is in an expanded condition, as shown in FIG. 4b. In other embodiments, the distal section 130 includes an annular balloon or other inflatable element 173 as shown in FIG. 5a that expands with the introduction of a pressurized gas or fluid, as shown in FIG. 5b. In any embodiment of the present invention, the distal end 130 may include elements that comprise a shape memory material as known in the art, such as a one-way or two-way shape memory polymer or metal that expands the distal section upon the application of heat from the unexpanded condition to the expanded condition. In other embodiments, the distal end 130 does not include any shape memory materials, but will expand to its expanded condition upon the application of force from advancement of the implant or from another external force, such as by the annular balloon shown in FIG. 5.

In one embodiment of the present invention, when the distal section 130 is in an unexpanded condition, its cross-sectional outer dimension is preferably less than about 1.0 millimeter, and more preferably less than about 0.8 millimeter, to facilitate entry into small body spaces such as the uterotubal junction. This is in comparison with the dimensions of typical implants used for placement within the uterotubal junction for sterilization purposes, which are preferably within the range of 1.0-2.0 mm, and usually about 1.6 mm, in diameter. As such, the cross-sectional inner and outer dimensions 112, 113 of the proximal section 110 is preferably within the range of 1.2-2.2 millimeters, and 1.3-2.3 millimeters, respectively. For the sterilization application, the length of the expandable distal section 130 are about 3-20 millimeters, and preferably about 5-15 millimeters, which represents the distance within the fallopian tube beyond the uterotubal junction at which the implant 160 is preferably delivered.

The delivery device 100 preferably includes one or more electrodes, such as longitudinal electrodes 180, preferably placed at regular intervals around a circumference of the distal section 130. Electrodes 180 are made from any suitable electrically conductive material such as stainless steel, copper, nickel-cobalt alloys, platinum, titanium, and nickel-titanium alloys. Electrodes 180 are configured for the delivery of radiofrequency (RF) energy or other suitable energy form, such as microwave energy, to surrounding tissue as part of a procedure that includes the delivery of implant 160 to the body of a patient. The energy may be supplied by any one of numerous energy generators available commercially. The electrodes 180 may be of any other suitable configuration that allow for the expansion of the distal section 130, such as zig-zag configurations, point electrodes applied by conductive ink, or needle electrodes, for example.

In the example of implant delivery for female sterilization, the implant 160 is loaded into the proximal section 110 followed by advancing the implant using a push rod 190 or similar instrument, as shown in FIGS. 2 and 3. In one embodiment, multiple implants 160 are loaded into the proximal section 110 for delivery into the body of a patient. The loaded delivery device is then packaged, sterilized using ethylene oxide gas, for example, and then shipped and stored until use. When ready for use, the delivery device 100 is removed from its packaging materials and, in this example, is inserted through the vagina, through the cervix, and into the uterus. Such insertion may be done under x-ray guidance, sonographically, hysteroscopically, or in the absence of visualization, and may be conducted under general and/or local anesthesia. The distal end 130 of the delivery device 100 is inserted through the uterotubal junction and into the fallopian tube. Once at this location, in a preferred embodiment, RF energy is delivered to the electrode(s) 180. The distal section 130 is expanded either before or after energy delivery via the electrode(s) 180.

Subsequent to energy delivery, or alternatively in the absence of any energy delivery, the distal section 130 is expanded as previously discussed, and the implant 160 is concurrently or subsequently released from the delivery device 100 by the relative movement between a contact member 190 and the delivery device 100. In an exemplary embodiment, the contact member 190 may be inserted into the proximal section 110 to contact the implant 160 and push it into the distal section 130, as shown in FIG. 2. Alternatively, the contact member 190 is held stationary, and the delivery device 100 may be withdrawn in a proximal direction such that the contact member is released from the delivery device 100 through the opening 134 and into the patient. The contact member 190 is made from any suitable material that provides sufficient column stiffness to rigidly engage the implant 160 such that it enters the distal section 130 and exits the opening 134. Examples of such materials include tubes or wires made from stainless steel or nitinol. In a preferred embodiment, the distal end of the contact member 190 is coated with polyurethane or other polymeric material to minimize the risk of damaging the implant 160 upon contact with the contact member 190.

Following delivery of the implant 160, the distal section 130 is preferably reduced to its unexpanded condition and removed from the patient. The deployed implant 160 is left within the patient to allow for tissue ingrowth and subsequent permanent occlusion of the fallopian tube. The process is preferably repeated for each fallopian tube. As an aid to long term retention, the implant is porous as previously discussed to facilitate tissue ingrowth.

The delivery device 100 of the present invention is manufactured using known fabrication techniques and materials. For example, the portions of the delivery device 100 may be manufactured by extruding polymeric tubes made from any suitable material, such as, for example, polyurethane or polyether block amide such as PEBAX® (Arkema France Corporation, Colombes, France). In a preferred embodiment, an outer jacket of a relatively stiff material, such as polyetheretherketone, is applied over the proximal section 110 of the device 100, as an extrusion. The expandable portion of the device 100 is manufactured using known techniques, whether by braiding polymer or metallic strands, manufacturing polymeric balloons, or cuffing slits or slots into the side wall 150 of the distal section 130 as described for the preferred embodiments herein. If made from a different material from the proximal section 110 and optional intermediate section 120, the distal section 130 is attached using known techniques, such as bonding by adhesion, co-extrusion, joining by application of heat and/or pressure, or the like.

The present invention provides for the delivery of implants into small bodily spaces with advantages not heretofore known. Although the present invention is described with specific reference to an occlusive implant that is placed within the fallopian tubes for sterilization purposes, it is intended that the present invention be applicable to any implant for delivery into small bodily spaces. Furthermore, it will be apparent to those skilled in the art that various modifications and variations can be made in the structure and methodology of the present invention. It is intended that the present invention cover the modifications and variations of this invention provided that they come within the scope of the appended claims and their equivalents.

We claim:

1. A fallopian tube occlusion assembly, comprising:
   an implant;
   an elongated member defining an axial lumen, the elongated member comprising a non-expandable proximal portion and an expandable distal portion, the expandable distal portion comprising a side wall opening in communication with the lumen;
   said expandable distal portion having a first cross-sectional outer dimension and a first cross-sectional inner dimension when in an unexpanded condition, and a second cross-sectional outer dimension and a second cross-sectional inner dimension when in an expanded condition, said second cross-sectional outer dimension being greater than said first cross-sectional outer dimension, and said second cross-sectional inner dimension being greater than said first cross-sectional inner dimension;
   wherein said first cross-sectional inner dimension of said expandable distal portion is less than a cross-sectional dimension of the implant; and
   wherein the assembly is configured for movement of the implant within said lumen and for delivery of the implant into a fallopian tube through the side wall opening of the expandable distal portion.

2. The assembly of claim 1, wherein said non-expandable proximal portion has a substantially constant cross-sectional inner dimension and a substantially constant cross-sectional outer dimension.

3. The assembly of claim 2, wherein said second cross-sectional inner dimension of said expandable distal portion comprises a substantially same dimension as said cross-sectional inner dimension of said non-expandable proximal portion.

4. The assembly of claim 1, wherein said first cross-sectional outer dimension of said expandable distal portion is less than 1.0 millimeter.

5. The assembly of claim 4, wherein said first cross-sectional outer dimension of said expandable distal portion is up to 0.8 millimeters.

6. The assembly of claim 1, wherein said expandable distal portion comprises a shape memory material.

7. The assembly of claim 6, wherein said shape memory material is nitinol.

8. The assembly of claim 1, wherein the expandable distal portion further comprises an electrode.

9. The assembly of claim 8, wherein said electrode comprises a longitudinal element.

10. The assembly of claim 1, wherein said expandable distal portion comprises a longitudinal length 10.0 millimeters to 20.0 millimeters.

11. The assembly of claim 1, wherein said expandable distal portion is configured to be disposed or positioned in a fallopian tube.

12. The assembly of claim 1, wherein said expandable distal portion comprises a braided tube.

13. The assembly of claim 1, wherein said expandable distal portion comprises a ball tip distal end.

14. The assembly of claim 1, wherein said expandable distal portion is more flexible than said non-expandable proximal portion.

15. The assembly of claim 1, wherein said expandable distal portion is configured to contact an inner surface of a fallopian tube when in an expanded condition.

16. A fallopian tube occlusion assembly, comprising:
an implant;
an elongated member defining an axial lumen, the elongated member comprising a non-expandable proximal portion and an expandable distal portion, the expandable distal portion comprising a side wall opening in communication with the lumen;
said expandable distal portion comprising a braided structure and having a first cross-sectional outer dimension and a first cross-sectional inner dimension when in an unexpanded condition, and a second cross-sectional outer dimension and a second cross-sectional inner dimension when in an expanded condition, said second cross-sectional outer dimension being greater than said first cross-sectional outer dimension, and said second cross-sectional inner dimension being greater than said first cross-sectional inner dimension;
an electrode disposed in the expandable distal portion;
wherein said first cross-sectional inner dimension of said expandable distal portion is less than a cross-sectional dimension of the implant; and
wherein the assembly is configured for movement of the implant within said lumen and for delivery of the implant into a fallopian tube through the side wall opening of the expandable distal portion.

* * * * *